United States Patent [19]
Grant

[11] Patent Number: 5,380,293
[45] Date of Patent: Jan. 10, 1995

[54] INTRAVENOUS INFUSION SET

[76] Inventor: Graham C. Grant, 19 Lockley Parade, East Roseville, New South Wales, 2069, Australia

[21] Appl. No.: 190,641

[22] Filed: Feb. 2, 1994

[30] Foreign Application Priority Data

Feb. 3, 1993 [AU] Australia ............... PL7085

[51] Int. Cl.$^6$ .............. A61M 5/32; A61M 25/02; A61M 25/00
[52] U.S. Cl. ................ 604/177; 604/283
[58] Field of Search ........... 604/283, 177, 171, 158, 604/165, 180, 179

[56] References Cited

U.S. PATENT DOCUMENTS

| | | | |
|---|---|---|---|
| 2,389,355 | 11/1945 | Goland et al. | 604/165 |
| 3,769,975 | 11/1973 | Mimoy et al. | 604/177 |
| 3,792,703 | 2/1974 | Moorehead | 604/158 |
| 4,160,450 | 7/1979 | Doherty . | |
| 4,170,993 | 10/1979 | Alvarez . | |
| 4,349,072 | 9/1982 | Ishikawa | 604/177 |
| 4,362,156 | 12/1982 | Feller, Jr. et al. | 604/177 |
| 4,388,074 | 6/1983 | Sakara et al. | 604/177 |
| 4,676,783 | 6/1987 | Jagger et al. | 604/177 |
| 4,747,831 | 5/1988 | Kulli . | |
| 4,772,264 | 9/1988 | Cragg | 604/179 |
| 4,969,876 | 11/1990 | Patterson | 604/177 |
| 5,141,497 | 8/1992 | Erskine | 604/177 |
| 5,149,328 | 9/1992 | Zaha | 604/177 |
| 5,192,275 | 3/1993 | Burns | 604/177 |

FOREIGN PATENT DOCUMENTS

| | | |
|---|---|---|
| 0566769 | 10/1993 | European Pat. Off. . |
| 0475857 | 3/1992 | France . |
| 2034185 | 6/1980 | United Kingdom . |
| 2248021 | 3/1992 | United Kingdom . |
| WO92/08502 | 5/1992 | WIPO . |

Primary Examiner—Paul J. Hirsch
Attorney, Agent, or Firm—Davis, Bujold & Streck

[57] ABSTRACT

An intravenous infusion set for administering drugs to a patient, typically in an operating theatre or under intensive care conditions. The infusion set is of the winged needle type and it has been developed with the object of reducing the risk of so-called needlestick injury for medical professionals. The infusion set incorporates a hypodermic needle to which infusant is delivered and the needle is located within a small diameter cannula in the form of a plastics material sleeve which is intended to be inserted into a patient's vein. The needle is slidable axially between two limiting positions within the sleeve such that, when in a first of the positions, a sharp tip end of the needle projects beyond the sleeve and, when in the second position, the sharp tip end of the needle is retracted relative to the sleeve and is located wholly within the sleeve. In use of the infusion set, after the needle has been inserted into a vein the tip end of the needle is retracted into and remains within the sleeve.

4 Claims, 3 Drawing Sheets

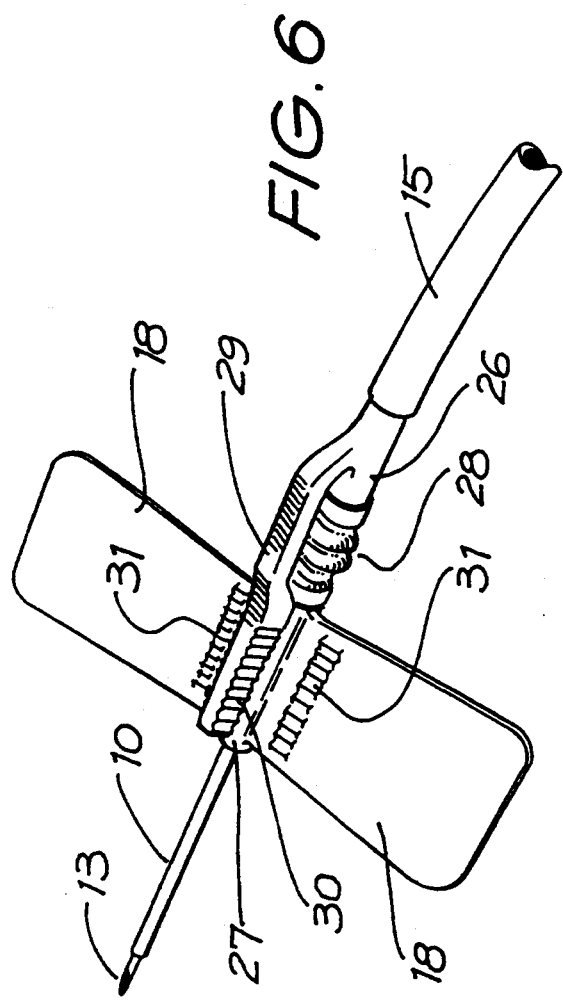
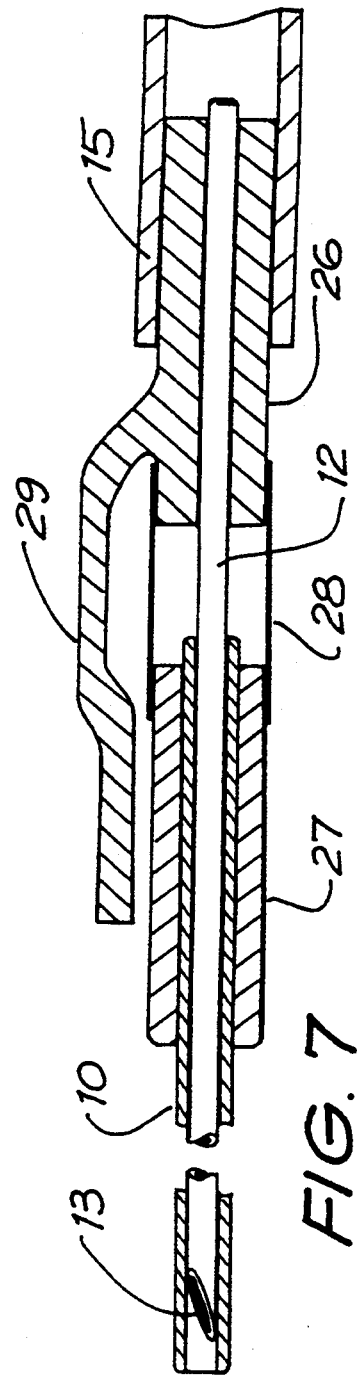

INTRAVENOUS INFUSION SET

FIELD OF THE INVENTION

This invention relates to an intravenous infusion set for medical use and, in particular, to an infusion set which provides for a reduced possibility of needlestick injury during use of the infusion set. The invention has particular application to infusion sets of the winged needle type but does have more general application.

BACKGROUND OF THE INVENTION

Whilst needlestick injuries have always presented a problem to the medical profession, the problem has become significantly greater as a result of the current prevalence of Human Immunodeficiency Virus (HIV) and the acute cross-infection risks that are inherent in treating HIV affected patients. Consequently, there is now a greater responsibility on institutions that employ medical and paramedical personnel to provide equipment that is as safe as possible when used routinely in the treatment of patients, both in operating theatre and ward situations. However, there is also a conflicting pressure to which medical institutions are subject, that is a pressure to reduce expenditure and to minimise costs in relation to both medical equipment and human resources. Therefore, in the context of intravenous infusion sets, which are used extensively in hospitals, there is a need to provide devices that are safe to use and are inexpensive to produce.

SUMMARY OF THE INVENTION

The present invention seeks to meet this need by providing an intravenous infusion set which comprises a hypodermic needle, a length of flexible tubing connecting with the needle and arranged in use for delivering liquid to the needle, and a sleeve in which the needle is located. The needle is slidable axially between two limiting positions within the sleeve. When in a first of the positions, a sharp tip end of the needle projects beyond the sleeve to facilitate insertion of the sleeve into a person's vein and, when in the second position, the sharp tip end of the needle is retracted relative to the sleeve and is located wholly within the sleeve.

When using the infusion set and inserting it into a patient, the needle is first moved to the first position, in which the sharp tip end of the needle projects ahead of the sleeve. The needle is then held in that position whilst the sharp tip end of the needle and the sleeve are inserted into the patient's vein. Thereafter, the needle is retracted to the second position and the infusion set is taped or otherwise held in position on the patient with the tip end of the needle in its retracted position. When the infusion set is to be disconnected from the patient, the entry point to the patient's vein is covered with a pad or the like and the infusion set is then released from the patient. Because the sharp tip end of the needle has previously been retracted to the second position, the attending medical practitioner or paramedic will be protected against needlestick injury which might otherwise arise from unexpected movement of the patient and/or elastic movement of the infusion set.

The hypodermic needle may be held in the first position in one of two ways whilst it is being inserted into a patient's vein. It may be clamped relative to the sleeve by the person who is fixing the infusion set in place, so as to prevent the needle from sliding relative to the sleeve. Alternatively, a releaseable detent or friction locking arrangement may be provided between the sleeve and the needle to hold the needle in the first and second positions relative to the sleeve.

A transversely extending wing-like strip of plastics material preferably is secured to the sleeve to facilitate attachment of the infusion set to the patient.

The invention will be more fully understood from the following description of alternative embodiments of the invention. The description is provided by way of example with reference to the accompanying drawings.

BRIEF DESCRIPTION OF THE DRAWINGS

FIG. 6 illustrates a perspective view of a third embodiment of the infusion set with a hypodermic needle shown projecting ahead of a containing sleeve; and FIG. 7 shows on an enlarged scale a sectional elevation view of the embodiment of FIG. 6 but with the hypodermic needle in a retracted position relative to the containing sleeve.

DETAILED DESCRIPTION OF THE INVENTION

Figure 1:
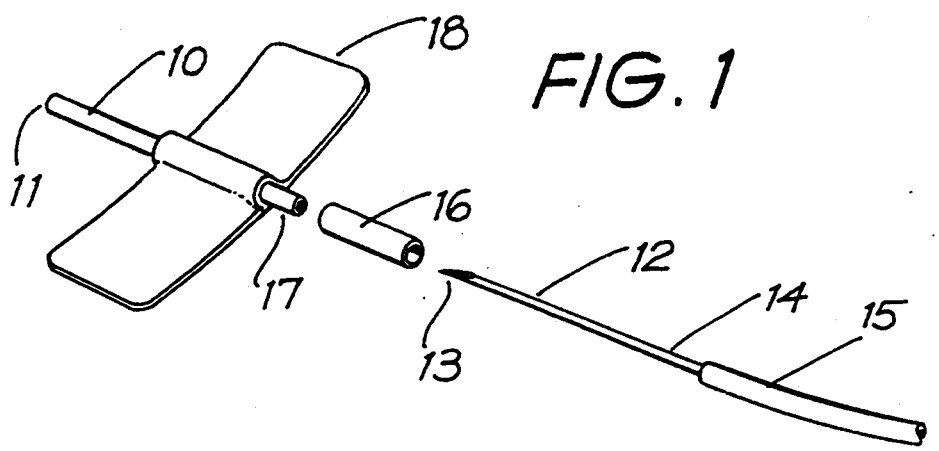
FIG. 1 shows an exploded view of the component parts of the "patient end" of a first infusion set embodiment.
Figure 2:
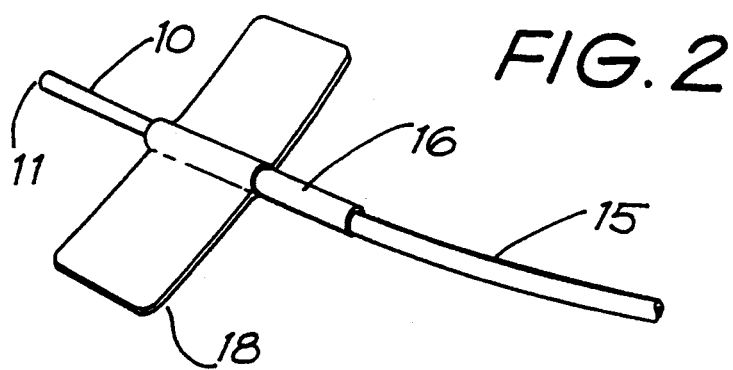
FIG. 2 shows the infusion set of FIG. 1 but with the various component parts assembled and with a hypodermic needle component in a retracted position relative to a containing sleeve.
Figure 3:
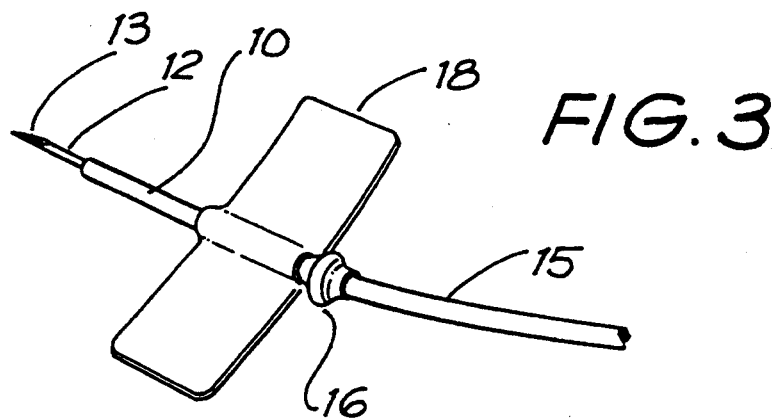
FIG. 3 shows a further view of the infusion set of FIG. 1 but with the hypodermic needle in a forwardly projecting position relative to the containing sleeve.

As shown in FIG. 1, the infusion set comprises a sleeve 10 in the form of a length of plastics material tube, the sleeve having a blunt forwardly projecting end 11. A hypodermic needle 12 having a sharp tip end 13 and the usual axial bore is located within the sleeve and is slidable between two positions. When in the first position, as indicated in FIG. 3, the sharp tip end 13 of the needle projects ahead of the sleeve 10 and is arranged to be inserted into a patient's vein. However, when in the second position, as indicated in FIG. 2, the sharp tip end 13 of the needle 12 is retracted relative to the sleeve 10 and is located wholly within the sleeve. When so located, the needle may not be inserted into a patient and nor may it stick accidentally into a person who is seeking to assist the patient.

The rearward end 14 of the needle 12 is connected permanently to a length of flexible delivery tubing 15 through which an infusant is in use delivered. Also, a thin-walled tube 16 which is formed from a flexible plastics material extends between and connects a rearward end portion 17 of the sleeve 10 and the delivery tubing 15. The tube 16 functions to determine the extent of movement of the needle 12 relative to the sleeve 10 and, thus, when the needle projects ahead of the sleeve 10 the tube 16 is caused to concertina to the condition shown in FIG. 3. When the needle 12 is fully retracted within the sleeve 10, the tube 16 straightens to the condition shown in FIG. 2.

A transversely extending wing-like strip 18 of plastics material is secured to the sleeve 10 to facilitate attachment of the infusion set to a patient.

Figure 4:
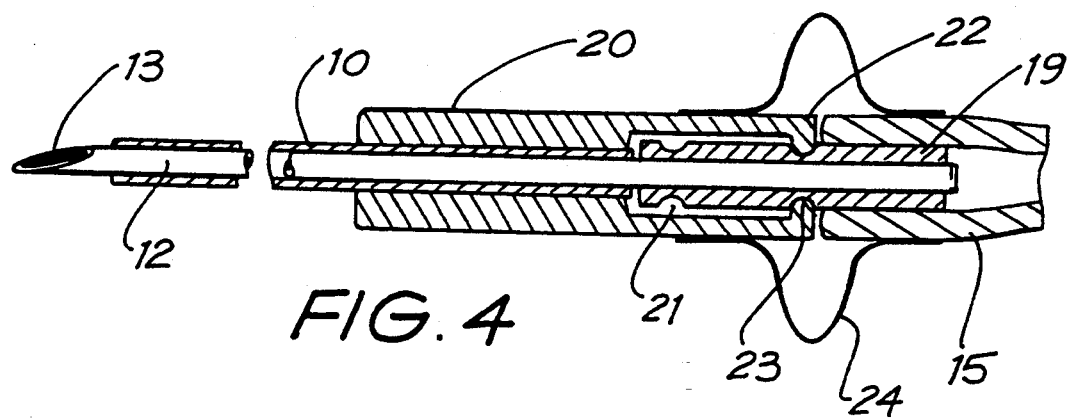
FIG. 4 shows a sectional elevation view on an enlarged scale of a portion of a second embodiment of the infusion set, with a hypodermic needle projecting ahead of a containing sleeve.
Figure 5:
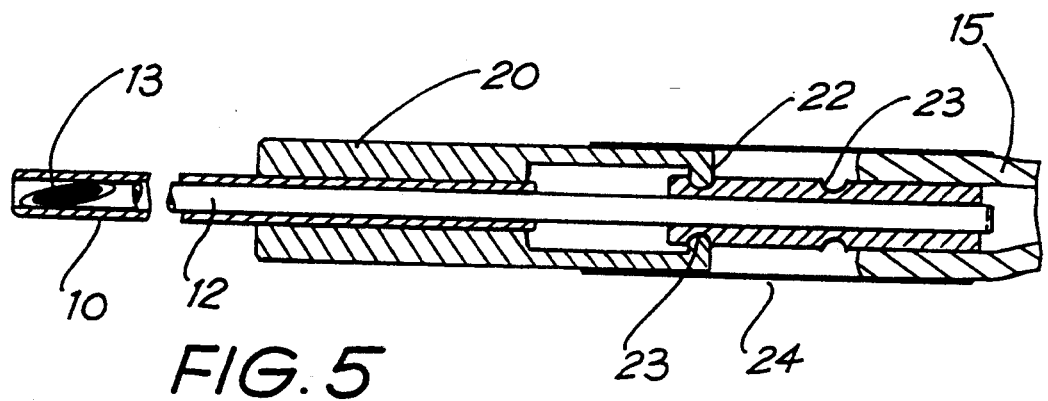
FIG. 5 shows the arrangement of FIG. 4 but with the hypodermic needle in a retracted position relative to its containing sleeve.

The embodiment of the invention which is illustrated in FIGS. 4 and 5 is similar to that which is shown in FIGS. 1 to 3 and like components are identified by like reference numerals. However, in the embodiment shown in FIGS. 4 and 5 a first body portion 19 is mounted to the rearward end of the needle 12 and is slidable axially within a second body portion 20, the latter being moulded integrally with or mounted to the sleeve 10. The first body portion 19 is formed with two axially spaced circumferentially extending grooves 21, and the extreme end 22 of the second body portion is formed with an inwardly directed flange 23 which is arranged to locate within one or the other of the grooves 21. One or the other or both of the first and second body portions 19 and 20 is or are formed from a resilient plastics material, so that the flange 23 locates positively and resiliently within one or the other of the grooves 21.

A deformable tube 24 optionally is provided to interconnect the sleeve 15 and the second body portion 20 of the device. The sleeve is moveable from a straight condition as shown in FIG. 5 when the needle 12 is retracted to a expanded position, as shown in FIG. 4, when the needle 12 projects from the sleeve 10.

As in the previously described embodiment, with the arrangement as shown in FIGS. 4 and 5, the needle 12 is first projected beyond the end of the sleeve 10 to permit insertion of the infusion set into a patient's vein. Thereafter, the needle 12 is retracted relative to the sleeve 10, so that when the device is removed from the patient the sharp tip end 13 of the needle is in a retracted condition and is not available to stick into the practitioner who is attending the patient.

In the embodiment of the invention which is shown in FIGS. 6 and 7, like reference numerals are again used to identify components which are present in the previously described embodiments. In the embodiment illustrated in FIGS. 6 and 7, a first body portion 26 is mounted to the rearward end of the hypodermic needle 12 and is slidable axially toward and away from a second body portion 27 through which the needle 12 projects. The second body portion 27 is moulded integrally with and forms a central body of the wing-like transversely extending strips 18. As in the previous arrangements, the strips 18 are used when taping or otherwise securing the end of the infusion set to a patient.

The second body portion 27 is moulded integrally with or mounted to the plastics material sleeve 10 through which the needle 12 extends. When the body portions 26 and 27 are spaced apart as shown in FIG. 7, the sharp tip end 13 of the needle 12 is wholly contained within the sleeve 10. When the body portion 26 is moved axially toward the body portion 27, the tip end 13 of the needle 12 is caused to project ahead of the sleeve 10, as shown in FIG. 6.

A piece of flexible (collapsible) tubing 28 connects the body portions 26 and 27, and the tubing 28 is caused to concertina as shown in FIG. 6 when the body portions 26 and 27 are moved toward one another and the tip end 13 of the needle 12 is caused to project ahead of the sleeve 10.

A bridging element 29 is moulded integrally with the first body portion 26 and projects ahead of the body portion 26 to overlie the second body portion 27. Opposite side walls of the bridging element are provided with serrations 30 and similar serrations 31 are formed on the transverse strips 18. The serrations 31 are positioned such that, when the strips 18 are folded upwardly in a direction toward one another and the strips 18 are pressed into contact with the side walls of the bridging element 29, the serrations 30 and 31 will interengage. Thus, when the first body portion 26 is moved toward the second body portion 27, the transverse strips 18 may be folded upwardly toward one another to sandwich the bridging element 29. Then, by gripping the transverse strips between ones forefinger and thumb, the first and second body portions 26 and 27 may be held in juxtaposed relationship with the tip end 13 of the needle 12 projecting ahead of the sleeve 10. When the tip end of the needle is projected from the sleeve 10 in this way the needle and containing sleeve 10 may be pushed into a persons vein whilst holding the transverse portion 18 in the manner described above. Thereafter, when the needle and sleeve have been inserted, the wing-like strips 18 are released to allow rearward movement of the first body portion 26 and consequential retraction of the needle 12 into the sleeve 10. The strips 18 may then be laid flat against and be taped to the patient to prevent unwanted retraction of the sleeve 10 from the vein.

I claim:

1. An intravenous infusion set comprising:

a hypodermic needle;

a length of flexible tubing being connected to one end of the needle for delivering an infusant liquid to the needle;

a second end of needle carrying a sharp tip, the second end of needle being housed inside a plastic material cannular sleeve, the needle being axially slidable relative to the sleeve between a first position, in which the sharp tip of the needle projects beyond the sleeve, and a second position in which the sharp tip of the needle is retracted and is located entirely within the sleeve;

a first body moulding connected to and moveable with the needle;

a second body moulding connected to the sleeve, the second body moulding being slidable relative to the needle whereby second body moulding is moveable in an axial direction toward and away from the first body moulding;

a bridge integrally formed with one of the first and the second body mouldings, and the bridge projecting in an overlying relationship with respect to the other one of the first and the second body mouldings; and transversely extending wing-like strips integrally formed with the other one of the first and the second body mouldings, the wing-like strips being foldable toward one another and being positioned, when so folded, to clamp the bridge therebetween once the first body moulding has sufficiently moved axially toward the second body moulding so that the wing-like strips, when folded toward one another, are able to hold manually the first body moulding and second body moulding in a juxtaposed relationship once the needle is in the first position, and thereafter the wing-like strips, during use of the infusion set, being moveable to lie flat against skin of a patient to facilitate fastening of the infusion set to the skin of the patient.

2. The intravenous infusion according to claim 1, wherein the sleeve is formed separately from and is fitted to the second body moulding.

3. The intravenous infusion according to claim 1, wherein said intravenous infusion set further comprises a collapsible tube interconnecting the first body moulding and the second body moulding with one another.

4. The intravenous infusion according to claim 1 wherein a portion of the bridge and a portion of the wing-like strips are each provided with serrations that are positioned to engage one another when the wing-like strips are folded toward one another to clamp the bridge therebetween.

* * * * *